United States Patent
Heldreth et al.

(10) Patent No.: US 6,942,670 B2
(45) Date of Patent: Sep. 13, 2005

(54) PROSTHESIS EVALUATION ASSEMBLY AND ASSOCIATED METHOD

(75) Inventors: Mark A. Heldreth, Mentone, IN (US); Deborah S. German, Plymouth, IN (US)

(73) Assignee: DePuy Orthopaedics, Inc., Warsaw, IN (US)

(*) Notice: Subject to any disclaimer, the term of this patent is extended or adjusted under 35 U.S.C. 154(b) by 169 days.

(21) Appl. No.: 10/017,617

(22) Filed: Dec. 14, 2001

(65) Prior Publication Data

US 2002/0082607 A1 Jun. 27, 2002

Related U.S. Application Data

(60) Provisional application No. 60/258,390, filed on Dec. 27, 2000.

(51) Int. Cl.$^7$ .............................. A61B 17/58; A61F 2/00
(52) U.S. Cl. ...................................................... 606/102
(58) Field of Search ........................... 623/11.11, 16.11, 623/18.11, 20.14, 20.15, 20.21, 20.22, 20.23, 20.27, 20.32, 23.39, 23.4, 23.42, 912, 914, 920, FOR 107, FOR 112, FOR 114, FOR 119; 606/102, 86, 53

(56) References Cited

U.S. PATENT DOCUMENTS

| 5,609,642 A | * | 3/1997 | Johnson et al. ............... 623/20 |
| 5,702,463 A | * | 12/1997 | Pothier et al. ................ 623/20 |
| 5,702,464 A | * | 12/1997 | Lackey et al. ................ 623/20 |
| 5,733,290 A | * | 3/1998 | McCue et al. ................ 606/86 |
| 5,733,292 A | | 3/1998 | Gustilo et al. |
| 5,782,925 A | | 7/1998 | Collazo et al. |
| 5,976,147 A | | 11/1999 | LaSalle et al. |
| 6,063,091 A | * | 5/2000 | Lombardo et al. ............ 606/88 |
| 6,206,928 B1 | * | 3/2001 | Colleran ..................... 623/20.3 |
| 6,214,052 B1 | * | 4/2001 | Burkinshaw ............. 623/20.34 |

FOREIGN PATENT DOCUMENTS

EP         0 780 093 A1     6/1997

* cited by examiner

*Primary Examiner*—Kevin Shaver
*Assistant Examiner*—Anu Ramana
(74) *Attorney, Agent, or Firm*—Maginot, Moore & Beck (57) ABSTRACT

A tibial trial assembly for evaluating the stability and kinematics of a tibial implant, particularly a mobile bearing implant, prior to committing to the final preparation of the proximal tibia is described. The tibial trail assembly includes a tray trial adapted to be secured onto a resected proximal end of a patient's tibia. An evaluation bullet is either adapted to removably fit into a configured recess in the trial tray, or is integral therewith. A trunnion on the evaluation bullet accepts a recess in a corresponding articular tibial insert trial. The tibial insert trial is thus received on the trunnion. Preferably, the evaluation bullet is removable from the trial tray such that the remaining assembly is used to locate and guide (orient) the instrument(s) that prepare the tibia for the final implant. Typically, this includes broaching, drilling, or punching through the opening in the trial tray/plate.

15 Claims, 12 Drawing Sheets

PROSTHESIS EVALUATION ASSEMBLY AND ASSOCIATED METHOD

PROVISIONAL PATENT APPLICATION

This application claims the benefit of U.S. Provisional Application Ser. No. 60/258,390, filed Dec. 27, 2000, the disclosure of such application being totally incorporated herein by reference in its entirety.

TECHNICAL FIELD OF THE INVENTION

The present invention relates generally to a surgical trial instrument assembly and, more particularly, to a method and apparatus for evaluating the stability and kinematic behavior of a mobile bearing knee implant prior to commitment to a final preparation of a proximal tibia.

BACKGROUND OF THE INVENTION

During the lifetime of a patient, it may be necessary to perform a joint replacement procedure on the patient as a result of, for example, disease or trauma. One such type of joint replacement procedure is a total knee replacement procedure in which a diseased and/or damaged knee joint is replaced with a prosthetic knee joint. A typical total knee replacement procedure utilizes a prosthesis that generally includes a femoral component, a tibial tray, and a tibial bearing insert. The femoral component generally includes a pair of laterally spaced apart condylar portions, the distal surfaces of which bear against a complementary pair of surfaces defined in the tibial bearing insert. The tibial tray typically includes a plate having a stem extending distally therefrom. The stem is implanted in a prepared medullary canal of the patient's tibia. Once implanted in such a manner, the tibial tray provides a surface on the proximal end of the tibia to which the tibial bearing insert may be affixed.

During performance of such a knee replacement procedure, the surgeon must evaluate the size and condition of the patient's bones (e.g. the patient's tibia) in order to determine the proper type and configuration of each of the various types of prosthetic components that are to be implanted. This procedure is known as trialing.

Surgeons prefer to check the stability and kinematic behavior of the implant prior to the final preparation of the tibia bone for the final implant. However, current trialing systems require the surgeon to prepare the bone for the final implant prior to checking the stability and behavior of the implant. In particular, current trialing systems require the proximal tibia to be broached, reamed, punched, or otherwise prepared in order to place an evaluation trial in place. This requires the surgeon to commit to the use of a mobile bearing tibial implant prior to being able to finish their evaluation of stability and kinematic behavior.

What is needed therefore is an apparatus and method for trialing a tibia implant.

What is further needed therefore is an apparatus and method for evaluating the stability and kinematic behavior of a mobile bearing knee implant during a total knee arthroplasty.

SUMMARY OF THE INVENTION

In accordance with one embodiment of the present invention, there is provided a trial tray assembly for evaluating the stability and kinematic behavior of a prosthetic knee implant prior to implanting the final prosthetic knee implant. The assembly includes a trial tray configured to be placed on a proximal end of a resected tibia, the trial tray having a plate with a configured opening. The assembly further includes an alignment handle detachably couplable to the plate. Moreover, the assembly includes an evaluation bullet having a profile corresponding in shape to the configured opening and removably received in the configured opening, the evaluation bullet including a trunnion adapted to receive a trial insert thereon, the trial insert mimicking the final prosthetic knee implant.

In accordance with another embodiment of the present invention, there is provided a method for evaluating the stability and kinematic behavior of a prosthetic knee implant prior to implanting a final prosthetic knee implant. The method includes the steps of (i) resecting a patient's proximal tibia, (ii) placing a trial tray onto the resected proximal tibia, the trial tray defined by a plate having a configured opening therein, (iii) placing an evaluation bullet into the configured opening, the evaluation bullet shaped to substantially conform to the configured opening and having a trunnion, (iv) placing an insert trial mimicking the final prosthetic knee implant having a recess therein onto the trunnion, and (v) moving the tibia to determine stability and kinematics of the insert trial.

In accordance with yet another embodiment of the present invention, there is provided an apparatus for evaluating the stability and kinematic behavior of a prosthetic knee implant before final implant of a prosthetic knee implant. The apparatus includes a trial tray having a configuration substantially corresponding to a shape of a resected tibia and including a cutout portion. The apparatus further includes a handle adapted to be removably attached to the trial tray. Moreover, the apparatus includes an evaluation bullet shaped to be removably received in the cutout portion and including a trunnion. Also, the apparatus includes a trial insert having a recess adapted to be removably received on the trunnion.

Pursuant to another embodiment of the present invention, there is provided a prosthesis evaluation assembly which includes a tray configured to be supported on a proximal end of a resected tibia, the tray having an opening defined therein. The prosthesis evaluation assembly further includes an evaluation member having (i) a lower portion configured to be received within the opening, and (ii) an upper portion configured to support a trial insert thereon.

In accordance with yet another embodiment of the present invention, there is provided a prosthesis evaluation assembly. The assembly includes a tray configured to be supported on a proximal end of a resected tibia, the tray having an opening defined therein. The assembly also includes an evaluation member having (i) a tray contact portion configured to be received within the opening, and (ii) an insert contact portion. In addition, the assembly includes a trial insert having a recess configured to receive the insert contact portion.

It is therefore an object of the present invention to provide a new and useful surgical assembly for evaluating the stability and kinematic behavior of a trial prosthetic implant prior to final prosthetic implant.

It is moreover an object of the present invention to provide an improved surgical assembly for evaluating the stability and kinematic behavior of a trial prosthetic implant prior to final prosthetic implant.

It is a further object of the present invention to provide a new and useful method of surgically evaluating the stability and kinematic behavior of a trial prosthetic implant prior to final prosthetic implant.

It is also an object of the present invention to provide an improved method of surgically evaluating the stability and kinematic behavior of a trial prosthetic implant prior to final prosthetic implant.

The above and other objects, features, and advantages of the present invention will become apparent from the following description and the attached drawings.

DETAILED DESCRIPTION OF THE INVENTION

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

It should initially be appreciated that the present invention is used after proper resection of a patient's proximal tibia for evaluating the stability and kinematics of a mobile bearing implant therefor prior to committing to the final preparation of the proximal tibia. Proper resection of the proximal tibia is beyond the scope of the present disclosure. Reference should be made to an appropriate surgical manual for such resection. In particular, reference is preferably made to the P.F.C.® Sigma Rotating Platform Knee System with M. B. T. Tray, copyright 2000, by DePuy International LTD, a Johnson & Johnson company, the disclosure of which is herein incorporated by reference in its entirety .

Figure 1:
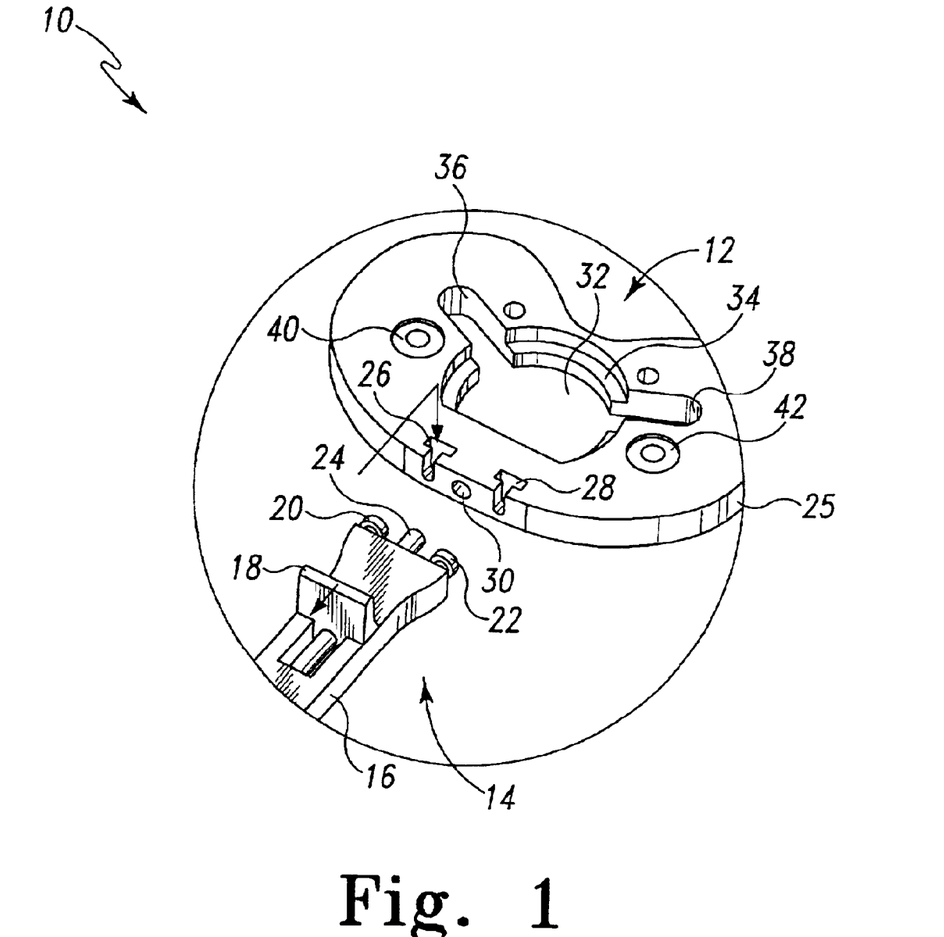
FIG. 1 is a perspective view of a trial tray and handle incorporating features in accordance with the principles of the present invention.

Referring now to FIG. 1, there is shown a trial tray assembly 10 having a trial tray 12 and a detachable alignment handle 14. The trial tray 12 has a body 25, preferably made of stainless steel, which is shaped to substantially correspond to the configuration of the patient's resected proximal tibia. The trial tray body 25 includes a cutout portion 32 that is partially surrounded by an inset ledge or rim 34. The cutout portion 32 includes a first radially extending slot 36 and a second radially extending slot 38. The inset ledge 34 is absent from the first and second radially extending slots 36 and 38. As explained further below, the cutout portion 32 and slots 36, 38 are configured and adapted to receive and retain an evaluation bullet.

The trial tray 25 also includes a first recessed bore 40 disposed proximate the slot 36 and a second recessed bore 42 disposed proximate the slot 38. The bores 40 and 42 are configured and adapted to receive fixation pins as explained below. In addition, the trial tray 25 includes a first slotted bore 26 in a sidewall thereof, and a second slotted bore 28 in the sidewall thereof. A third bore 30 is disposed between the first and second slotted bores 26 and 28. These bores are adapted and configured to receive pins or prongs of the alignment handle 14 as described below.

The alignment handle 14 is defined by a stem 16 having a first flanged pin or prong 20 and a second flanged pin or prong 22. The first and second flanged pins 20 and 22 are configured and adapted to be releasably received into the respective slotted bores 26 and 28 of the body 25 of the trial tray 12. The stem 16 also has a retractable center pin 24 that is configured and adapted to be received in the center bore 30 of the body 25 of the trial tray 12. A lever 18 controls the retraction and extension of the center pin 24.

For attachment of the handle 14 to the trial tray 12, the center pin 24 is retracted, and the flanged pins 20 and 22 are received into the slotted bores 26 and 28 respectively. Once the flanged pins 20 and 22 are received in the slotted bores 26 and 28, the center pin 24 is extended into the bore 30. The extension of the center pin 24 into the bore 30 prevents the flanged pins 20 and 22 from being removed from their respective slotted bores 26 and 28. The lever 18 and/or the center pin 24 are preferably biased into an extended position. Removal of the handle 14 from the body 25 is accomplished in a reverse manner to installation or attachment thereof.

Figure 2:
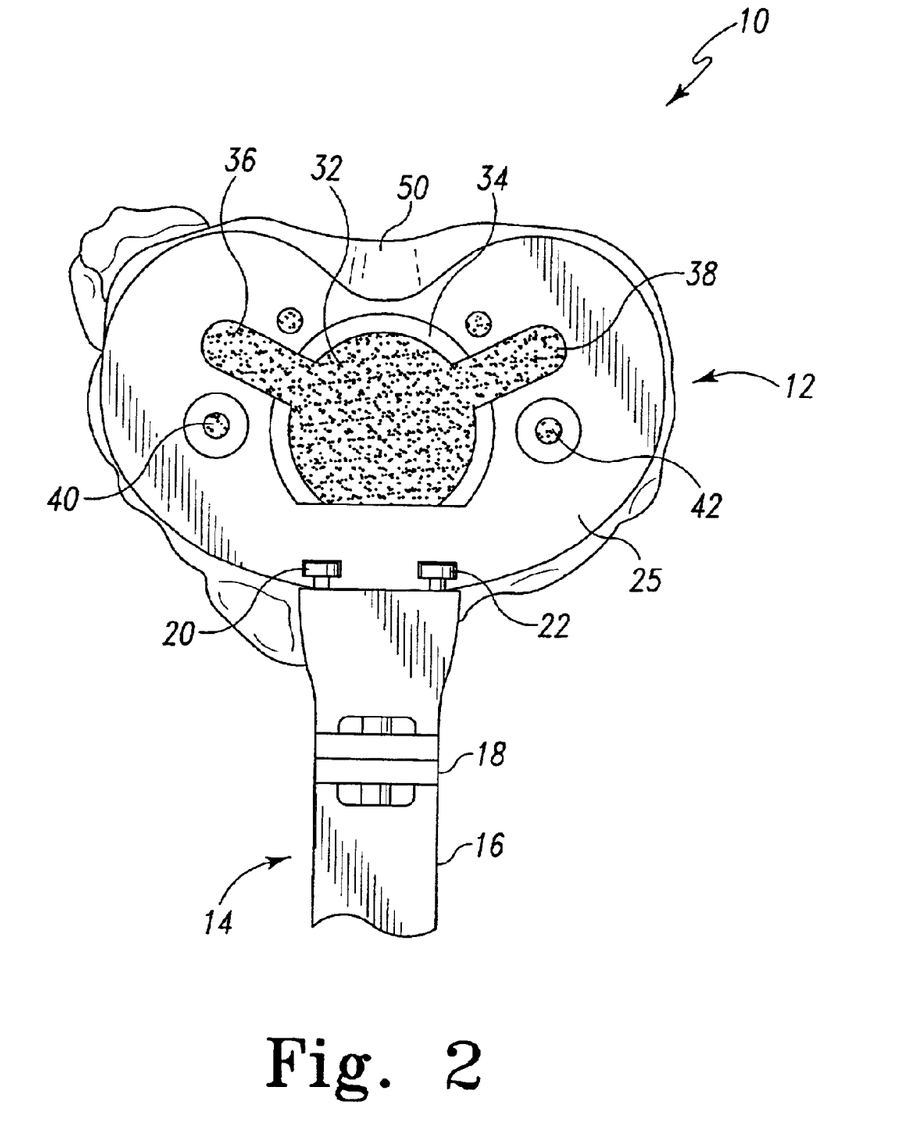
FIG. 2 is a top view of the trial tray and handle of FIG. 1 situated on a proximally resected tibia in accordance with the principles of the present invention.
Figures 3, 4, 5, 6, 7:
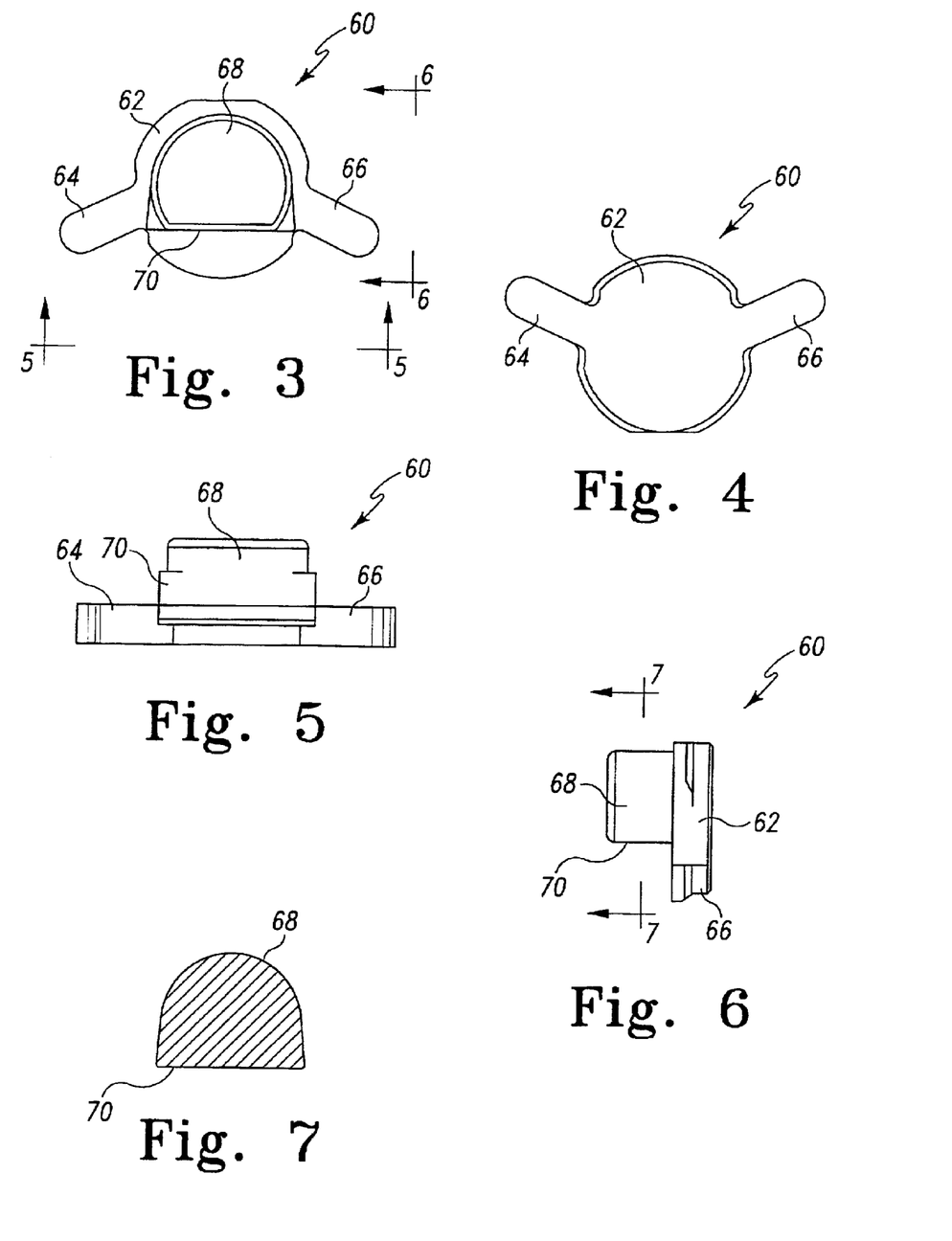
FIG. 3 is a top plan view of an embodiment of a lock-out evaluation bullet in accordance with the principles of the present invention.
FIG. 4 is a bottom plan view of the lock-out evaluation bullet of FIG. 3.
FIG. 5 is a side plan view of the lock-out evaluation bullet of FIG. 3 taken along line 5—5 thereof.
FIG. 6 is a side plan view of the lock-out evaluation bullet of FIG. 3 taken along line 6—6 thereof.
FIG. 7 is a sectional view of the trunnion of the lock-out evaluation bullet of FIG. 6 taken along line 7—7 thereof.
Figure 8:
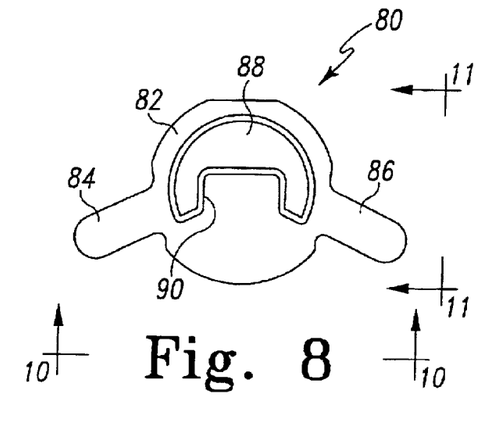
FIG. 8 is a top plan view of an embodiment of a pinned, rotational evaluation bullet in accordance with the principles of the present invention.
Figure 9:
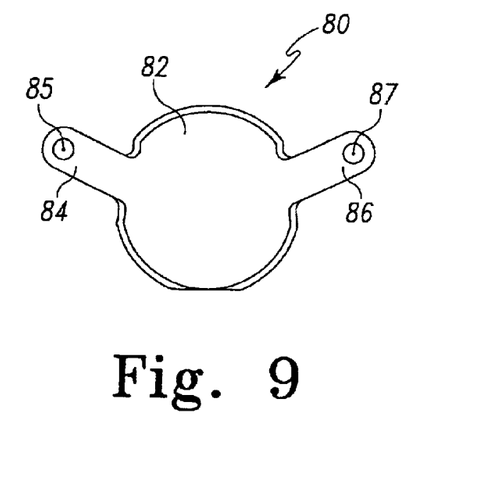
FIG. 9 is a bottom plan view of the pinned, rotational evaluation bullet of FIG. 8.
Figure 10:
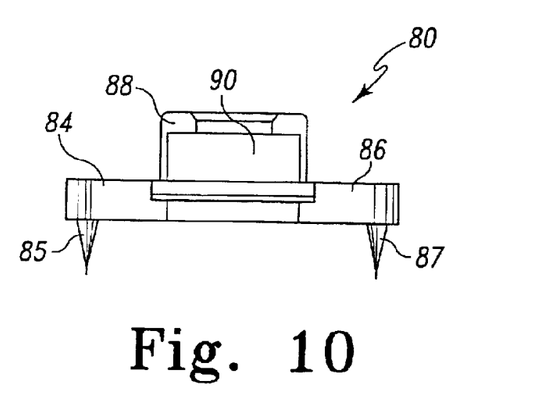
FIG. 10 is a side plan view of the pinned, rotational evaluation bullet of FIG. 8 taken along line 10—10 thereof.
Figure 11:
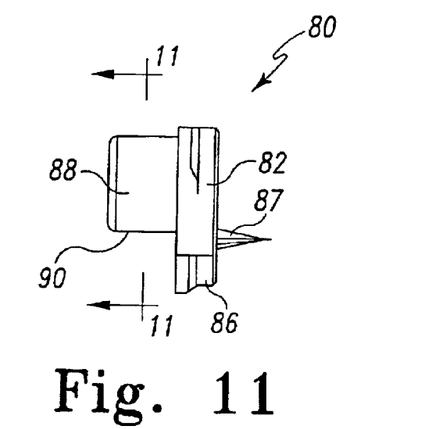
FIG. 11 is a side plan view of the pinned, rotational evaluation bullet of FIG. 8 taken along line 11—11 thereof.
Figure 12:
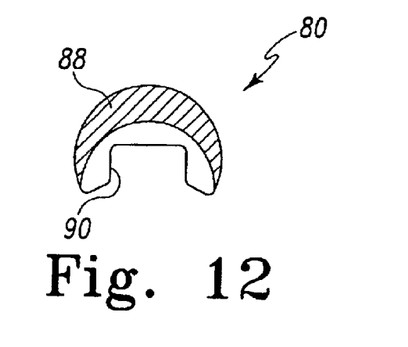
FIG. 12 is a sectional view of the trunnion of the pinned, rotational evaluation bullet of FIG. 11 taken along line 12—12 thereof.

Referring to FIG. 2, the trial tray assembly 10 is shown placed onto the patient's resected, proximal tibia 50. This is performed after resection of the proximal tibia, sizing of the trial tray 12, and attachment of the handle 14 to the trial tray 12. It should be appreciated that there are various sizes of trial trays to accommodate various sizes of a patient's tibia. Therefore, regardless of the size of the trial tray, the configuration and function is the same as described herein for each size. The surgeon must decide which trial tray best fits the patient's resected, proximal tibia. The trial tray 12 is now ready to receive an evaluation bullet.

Referring now to FIGS. 3–7, there is shown one embodiment of a tibia trial or evaluation bullet, generally designated 60, that may be used in conjunction with the trial tray assembly 10 during a total knee replacement surgery/operation. The evaluation bullet 60 is a fixed or non-rotation (lock-off) evaluation bullet. As explained further below, the evaluation bullet 60 is used with a non-rotatable insert trial.

The evaluation bullet 60 is preferably made of stainless steel and is defined by a body 62. The shape of the body 62 is substantially the same as the shape of the cutout portion 32 of the trial tray 12. The body 62 also has a first prong 64 and a second prong 66, each radially extending from therefrom in the same manner and substantially the same configuration as the slots 36 and 38 radially extend from the cutout portion 32. The body 62 further includes a trunnion 68 that defines a bearing surface for a trial insert 100 (see FIG. 14). The trunnion 68 is generally dome-shape in cross section and includes a flat 70 on one side thereof. The flat 70 provides the non-rotational component of the bearing surface.

Referring to FIGS. 8–12, there is shown another embodiment of a tibia trial or evaluation bullet, generally designated 80, that may be used in conjunction with the trial tray assembly 10 during a total knee replacement surgery/operation. The evaluation bullet 80 is a rotational evaluation bullet. As explained further below, the evaluation bullet 60 is used with a rotatable insert trial.

The evaluation bullet 80 is preferably made of stainless steel and is defined by a body 82. The shape of the body 82 is substantially the same as the shape of the cutout portion 32 of the trial tray 12. The body 82 also has a first prong 84 and a second prong 86, each radially extending from therefrom in the same manner and substantially the same configuration as the slots 36 and 38 radially extend from the cutout portion 32. The body 82 further includes a trunnion 88 that defines a bearing surface for a trial insert 110 (see FIG. 17). The trunnion 68 is generally arcuate-shaped in cross section and includes a concavity 90 on one side thereof. The concavity 90 provides a rotational bearing surface for the trial insert 110. The first prong 84 includes a first mounting spike 85 extending therefrom while the second prong 86 includes a second mounting spike 87. As explained further below, the spikes 85 and 87 temporarily affix the evaluation bullet 80 onto the resected tibia 50 in order to allow the trial insert 110 to rotate about the trunnion 88 by coaction between the trunnion 88/concavity 90 and the trial insert 110.

It should be appreciated that the two embodiments of the evaluation bullets 60 and 80 respectively shown in FIGS. 3–7, and 8–12, are for use during performance of a joint replacement procedure such as a total knee replacement procedure. Therefore, although the present invention is herein exemplarily described in regard to performance of a total knee replacement procedure, certain of the concepts of the present invention may be utilized in regard to replacement procedures at numerous other joint locations throughout the body.

Figure 13:
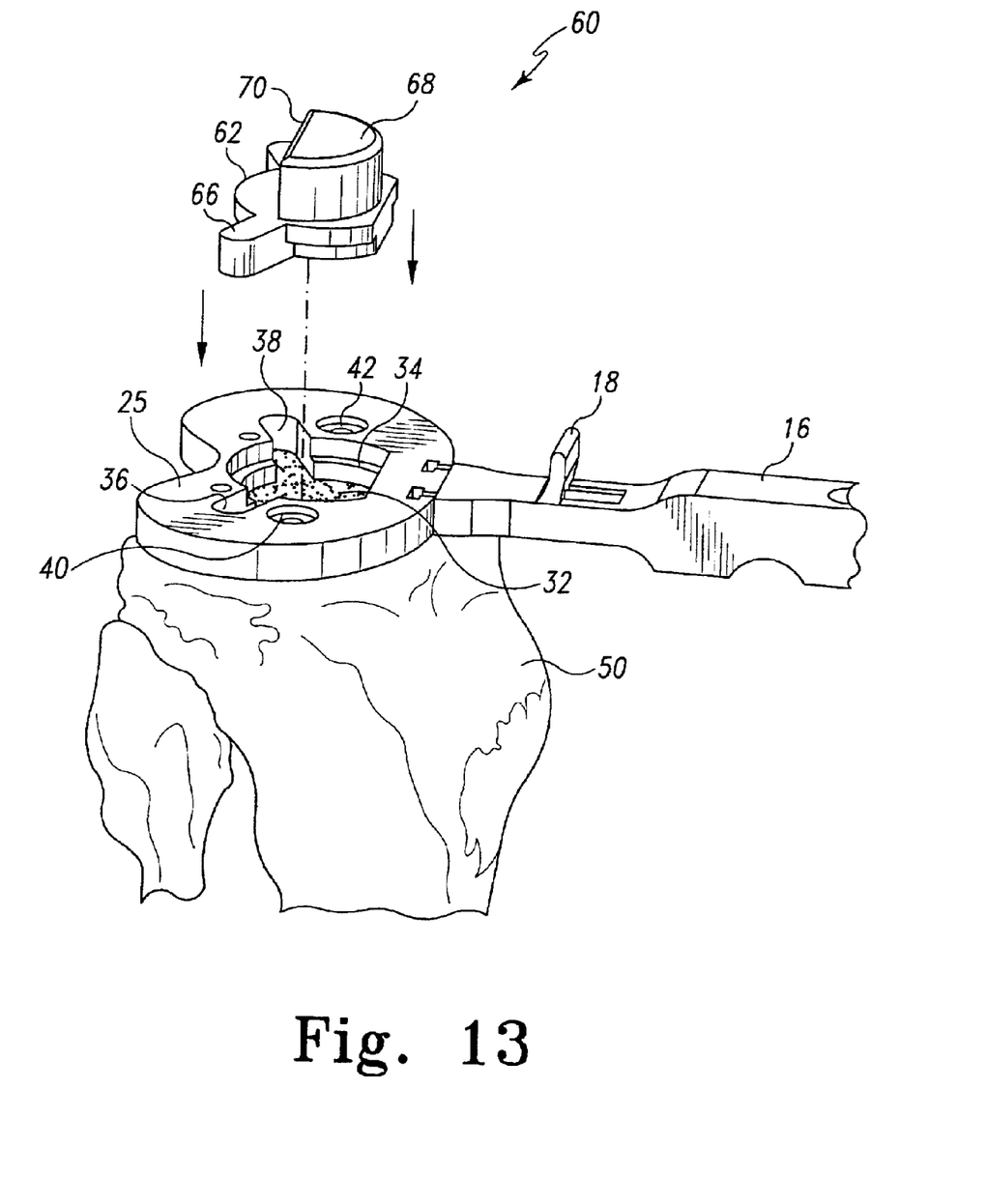
FIG. 13 is a front perspective view of the present trial tray and handle situated on the resected tibia and accepting the lock-out evaluation bullet.

Referring to FIG. 13, the evaluation bullet 60 is shown being inserted into the cutout portion 32 of the body 25 of the trial tray 12 after the trial tray assembly 10 is positioned onto the resected tibia 50. At this point, the trial tray assembly 10, which now includes the evaluation bullet 60, is ready to receive an insert trial that allows the surgeon to check the stability of the final implant.

Figure 14:
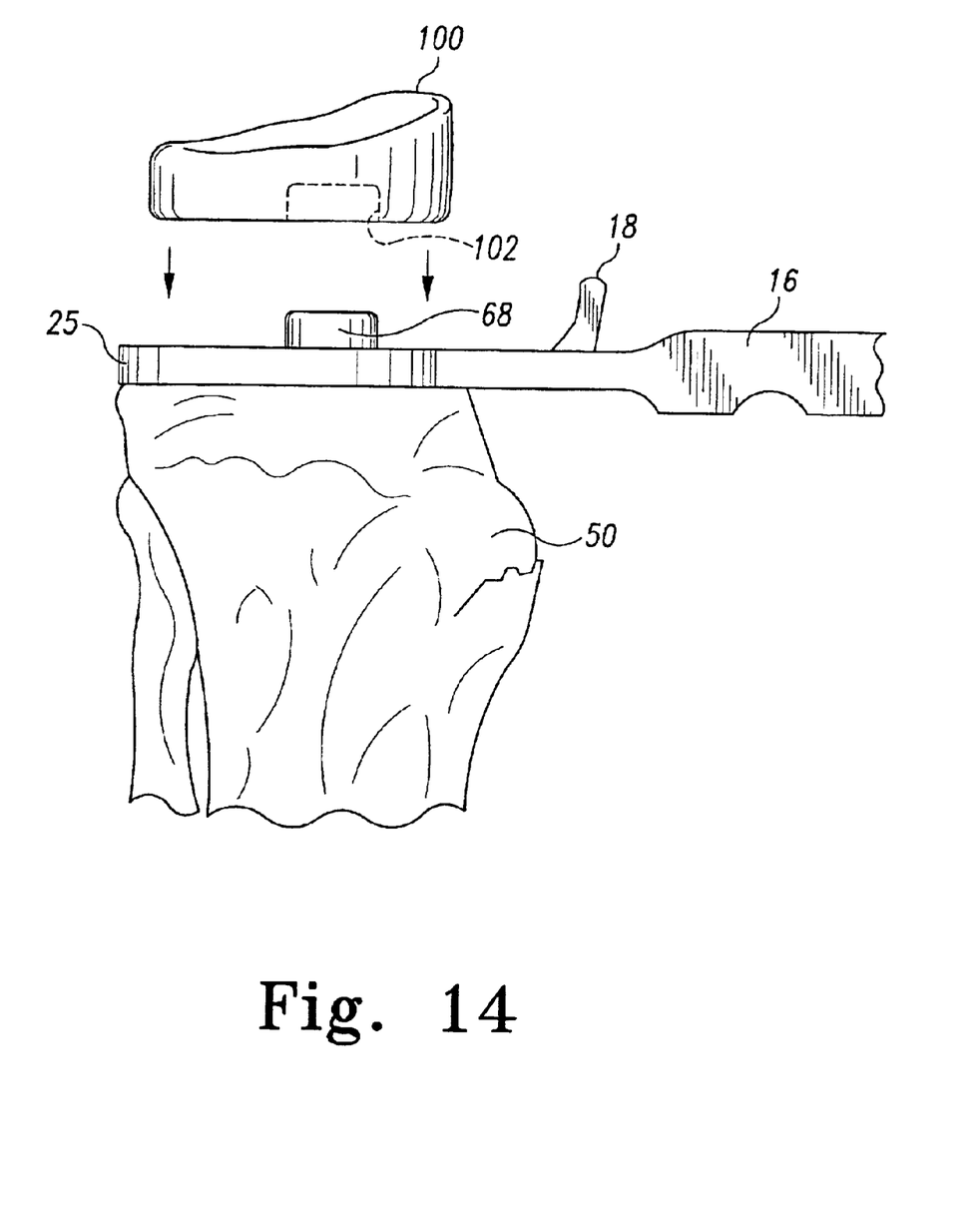
FIG. 14 is a side view of the present trial tray, handle and lock-out evaluation bullet of FIG. 13 on the resected tibia accepting a tibial insert trial.

Referring to FIG. 14, there is shown an insert trial 100 having a recess 102, being inserted onto the trunnion 68 of the evaluation bullet 60. The insert trial 100 is chosen to match the femoral size and style, and one that is either curved or stabilized, per the surgeon's preference. The recess 102 of the insert trial 100 is received on the trunnion 68 in a non-rotatable manner. When the insert trial 100 is in place, the knee of the patient is carefully extended, noting the anteroposterior stability, medial/lateral stability and overall alignment in the A/P and M/L plane. Various insert trials may be tried in order to ascertain which final implant will work best.

Figure 15:
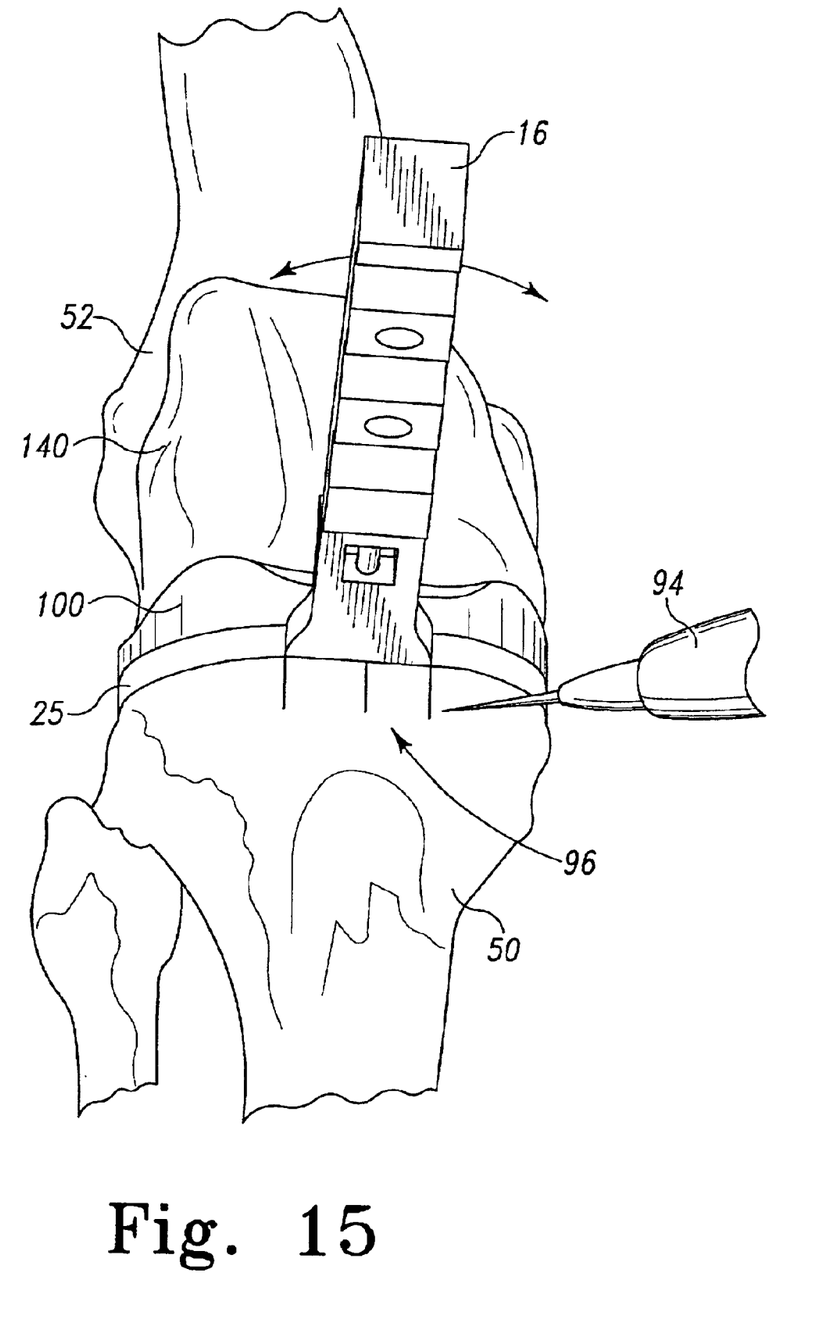
FIG. 15 is a front perspective view of the present trial tray, handle and lock-out evaluation bullet between the resected tibia and femur of FIG. 13 for rotational alignment thereof.

Referring to FIG. 15, rotational alignment of the tibial tray 25 is adjusted with the knee in full extension, using the handle 16 to rotate the tray 25 and insert trial 100 into congruency with the femoral trial 140. The rotation of the trial tray 25 is usually centered on the junction between the medial and central one-third of the tibial tubercle. Once the appropriate position is located, it is marked 96 by electrocautery tool 94 on the anterior tibial cortex. Overall alignment may be confirmed using a two part alignment rod, attaching it to the handle 16.

Figure 16:
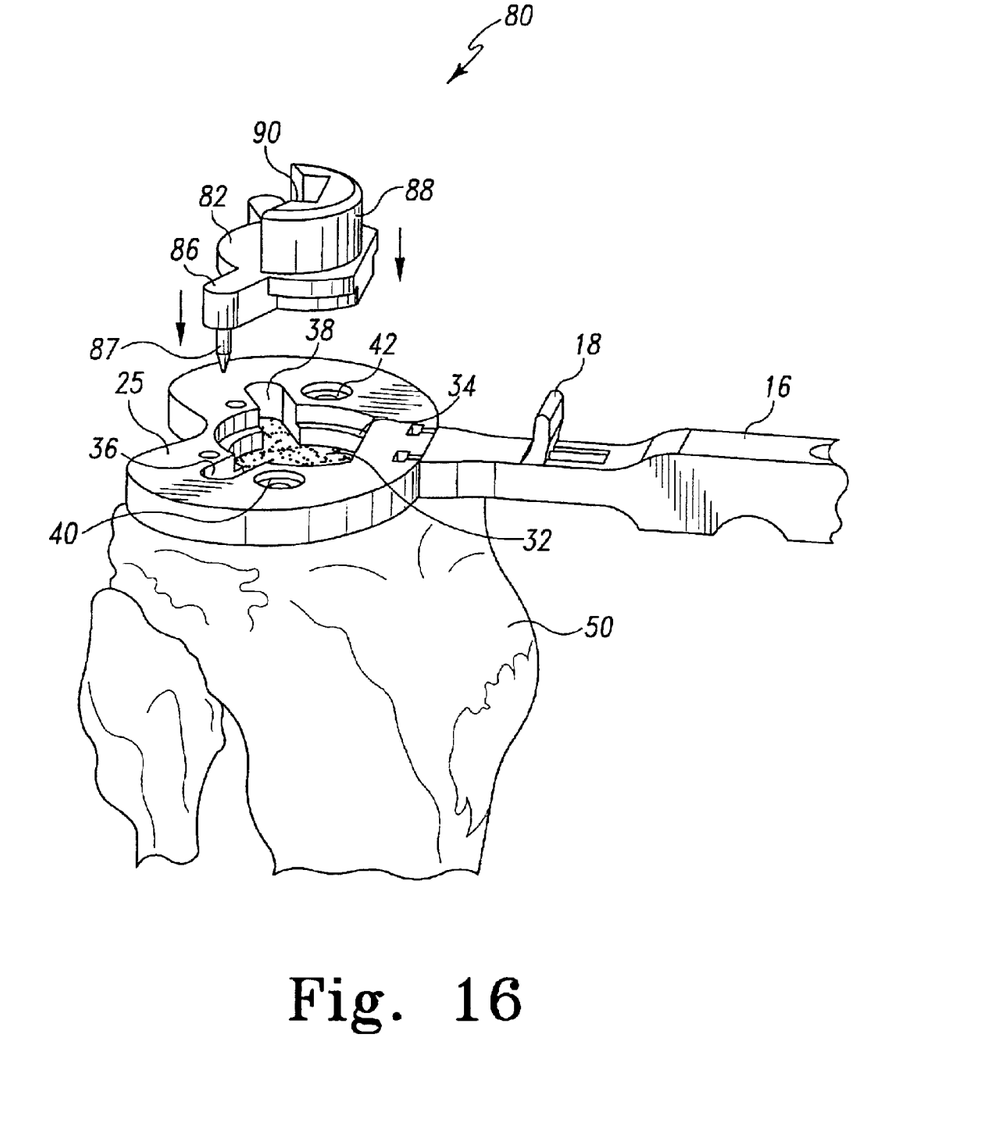
FIG. 16 is a front perspective view of the present trial tray and handle situated on the resected tibia and accepting the pinned, rotational evaluation bullet.

The trial reduction explained above with reference to a non-rotating insert trial, may be accomplished with a rotating insert trial instead of or in addition to the non-rotating insert trial. This is accomplished by using the evaluation bullet 80 (a "pinned" evaluation bullet) rather than the evaluation bullet 60. In this regard, reference is now made to FIG. 16. In FIG. 16, the evaluation bullet 60 is shown being inserted into the cutout portion 32 of the tray body 25 of the trial tray 12. The evaluation bullet 80 is tapped down to push the spikes 85 and 87 into the proximal tibia.

Figure 17:
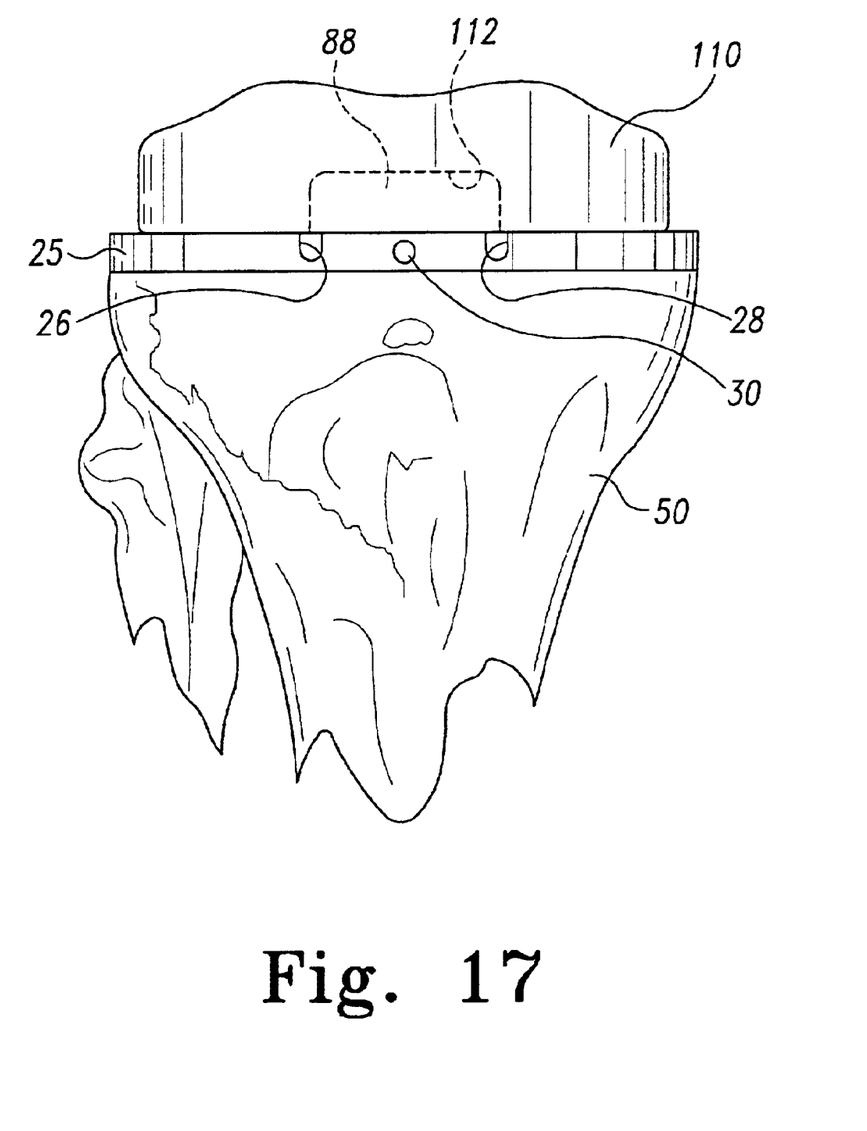
FIG. 17 is a front view of the present trial tray and tibial insert trial of FIG. 13 on the resected tibia.
Figure 18:
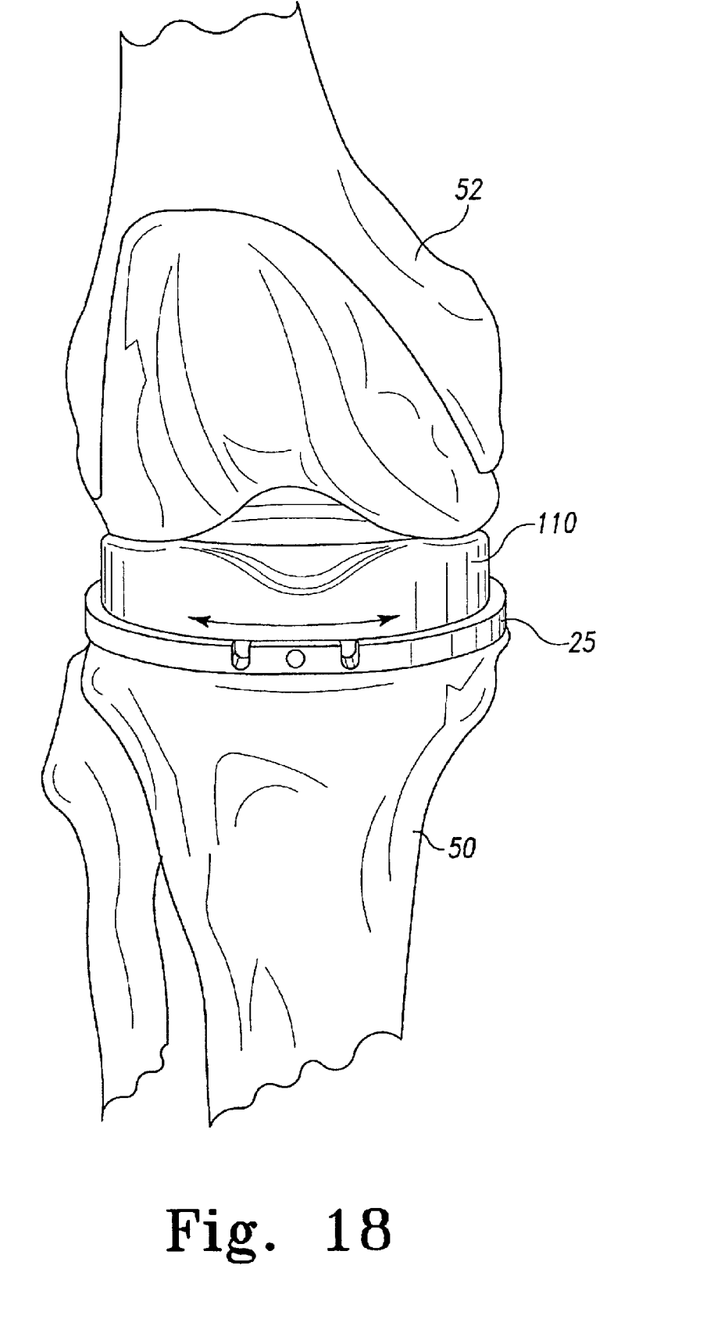
FIG. 18 is a front view of the present trial tray and tibial insert trial of FIG. 13 between the tibia and femur for evaluating rotation thereof.

Once the evaluation bullet 80 is in place, a tibial insert trial 110 is chosen that matches the chosen femoral size and style, curved or stabilized, as decided by the surgeon for the particular case and anatomy. Referring to FIGS. 17 and 18, the insert trial 110 includes a recess 112 that is received onto the trunnion 88 of the evaluation bullet 80. As well, the handle 16 is removed. With the trial insert 110 in place, the knee is extended noting the anteroposterior stability, medial/lateral stability and overall alignment in the A/P and M/L plane. Assessment of the bearing rotation and patellofemoral tracking can also be achieved, since the insert trial 110 is rotatable on the trunnion 88/evaluation bearing 80. Overall alignment can be confirmed using a two part alignment rod (not shown) attaching it to the handle 16 that would be reattached to the trial tray 25. If there is any indication of instability, a next greater thickness insert trial is selected and trial reduction is repeated. An insert trial should be selected which gives the greatest stability in flexion and extension while still allowing full extension. Once the correct insert trial is obtained, tray rotation and position is noted and marked with electrocautery.

Figure 19:
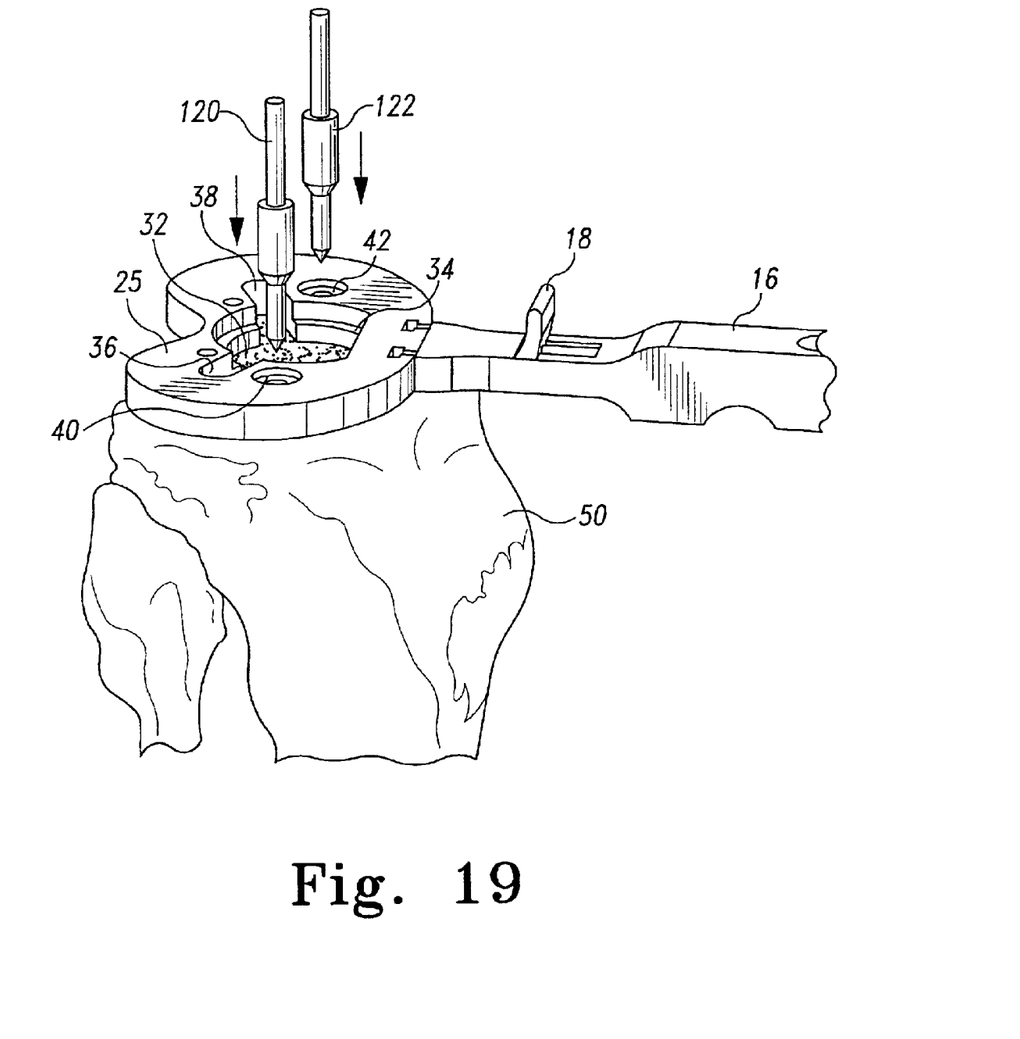
FIG. 19 is a perspective view of the present trial tray without an evaluation bullet being secured to the resected tibia for final implant.
Figure 20:
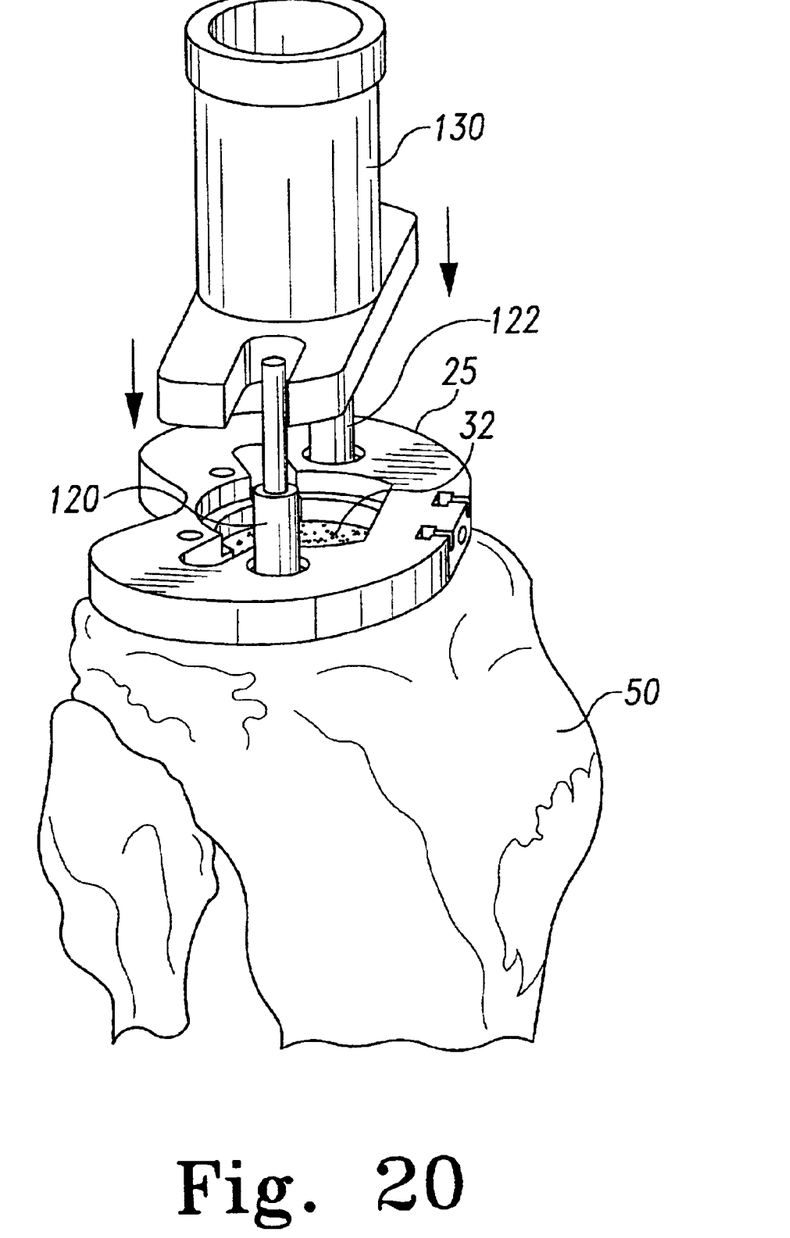
FIG. 20 is a perspective view of the trial tray secured onto the resected tibia showing placement of a drill guide thereon.

Referring to FIGS. 19 and 20, thereafter, the handle 16 is reattached to the tray 25 and the evaluation bullet is removed (for both evaluation bullets 60 and 80). The trial tray 12 is then secured to the tibia 50 by two fixation pins 120 and 122 respectively extending through recessed bores 40 and 42. The handle 16 is then removed and a drill guide 130 is retained thereon. Various options regarding the final implant vary from cemented to non-cemented applications, as well as with or without keel preparation. After drilling or the like, the trial tray 25 is removed and the final implant is installed.

Please note that the trunnion 88 of the evaluation bullet 80 is configured to cooperate with the structure of the insert trial 110 that defines the recess 112 so as to enable rotation of the insert trial 110 about a fixed axis relative to the evaluation bullet. However, it should be appreciated that the trunnion 88 of the evaluation bullet 80 and the structure of the insert trial 110 that defines the recess 112 may be alternatively configured. With such configuration, the alternatively configured trunnion would be configured to cooperate with the alternatively configured structure of the insert trial that defines the recess so as to enable some anterior-posterior movement (and/or medial-lateral movement) along with some rotational movement of the insert trial relative to the evaluation bullet.

Operation of the Present Invention

In operation, the trial tray assembly 10 of the present invention is utilized to evaluate and check the kinematics of a patient's tibia 50 for implantation of a tibial component during performance of a knee replacement procedure. In order to do so, the proximal end portion of the patient's tibia 50 is first resected by use of, for example, a bone saw (not shown). Thereafter, with the knee in maximal flexion, the patient's tibia 50 is subluxed anteriorly with a tibia retractor (not shown). An appropriately sized trial tray 12, having a handle assembly 14 is placed onto the resected tibia 50, as particularly shown in FIGS. 2, 13, and 16. In particular, a group of trial trays 12 may be provided which includes trial trays configured in a number of different sizes. Hence, a trial tray 12 which provides the greatest coverage of the resected surface of the tibia 50 without overhanging anteriorly of the midcoronal plane of the tibia 50 is selected from such a group.

An appropriate evaluation bullet 60 or 80 is selected and placed into the cutout portion 32 of the tray body 25. If a non-rotating insert trial is desired, the evaluation bullet 60 is chosen. If a rotating insert trial is desired, the evaluation bullet 80 is chosen. An appropriate insert trial is then placed onto the trunnion of the evaluation bullet. Once the bullet and insert trial are in place, the knee is extended in order to allow the surgeon to assess the medial and lateral stability of the knee along with the overall alignment of the knee in both the anterior/posterior and medial/lateral planes. If the surgeon encounters any potential instability, a different insert trial 100 or 110 may be substituted in order increase stability in flexion and extension along with allowing for full extension.

Moreover, during such a "mock up", the surgeon may adjust the rotational alignment of the trial tray 12 while the knee is positioned in full extension. The handle assembly 16 is utilized to rotate the trial tray 12 and the bearing insert 110 relative to the femoral component 140. Once each of the components associated with the prostheses is positioned in a desired location, the location of the trial tray 12 is marked so as to be recreated at a later time. In particular, as shown in FIG. 15, electrocautery is utilized to create a number of alignment marks 96 on the anterior tibial cortex of the patient's tibia 50. Such marks 96 correspond with features on the trial tray 12 and/or the handle assembly 16 thereby allowing the current orientation of the trial tray 12 to be reproduced by subsequent realignment of the trial tray 12 relative to the marks 96. Once the alignment marks 96 have been formed in the tibia 50, the trial prostheses may be disassembled or otherwise removed from the knee.

Thereafter, with the knee in substantially full flexion and the tibia subluxed anteriorly, the trial tray 12 is positioned in a desired rotational position by use of the alignment marks 96. Once aligned, the evaluation bullet is removed and the trial tray 12 is secured to the resected surface of the tibia 50 by use of the fixation pins 120, 122 which are inserted through the openings 40, 42 defined in the plate 25 of the trial tray 12. It should be appreciated that a pair of holes (not shown) may be drilled in the tibia 50 to receive the fixation pins 120, 122 prior to insertion thereof.

The handle assembly 16 which was utilized to align the trial tray 12 is then removed so that the handle assembly 16 associated with the drill guide 130 may be secured to the trial tray 12. Once the drill guide 130 has been secured to the trial tray 12, a bone drill (not shown) is advanced through an elongated bore of the drill guide 130 in order to drill a drilled hole in the patient's tibia 50. The bone drill (not shown) may be equipped with a depth stop which engages the body of the drill guide 130 once the bone drill has drilled to a desired depth in the patient's tibia 50. It should be appreciated that the drilled hole is provided to receive a sub-stem member of a final tibial component. As such, it should further be appreciated that the drilled hole is centered or otherwise aligned with the both the center of the plate 25 of the trial tray 12 (i.e. the center point of the plate opening 32) and the center of the tibia 50.

The trial tray 25 is used as a drill/broach guide and an appropriate bore is made in the tibia 50 for the final implant. Once broached or punched in such a manner, the trial assembly may be disassembled. The fixation pins 120, 122 may then be removed so as to allow the trial tray 12 to be detached from the tibia 50. The resultant features formed in the proximal end of the patient's tibia 50 are configured to receive a final tibial implant 100.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected. For example, while the evaluation bullet is disclosed as being adapted to removably fit into a configured recess in the trial tray, it is possible that the evaluation bullet can be made integral with the trial tray.

There is a plurality of advantages of the present invention arising from the various features of the present invention and associated method described herein. It will be noted that alternative embodiments of the surgical instrument assembly and associated method of the present invention may not include all of the features described yet still benefit from at least some of the advantages of such features. Those of ordinary skill in the art may readily devise their own implementations of a surgical instrument assembly and associated method that incorporate one or more of the features of the present invention and fall within the spirit and scope of the present invention as defined by the appended claims.

What is claimed is:

1. A prosthesis evaluation assembly, comprising:
   a tray configured to be supported on a proximal end of a resected tibia, said tray having an opening defined therein;
   an evaluation member having (i) a tray contact portion located within said opening when said tray contact portion is positioned in contact with a portion of said tray that surrounds said opening defined in said tray, and (ii) an insert contact portion, said evaluation member preventing advancement of a tool through said opening of said tray when said tray contact portion of said evaluation member is received within said opening, and further no portion of said evaluation member is positioned vertically below said opening defined in said tray when said tray contact portion is positioned in contact with said portion of said tray that surrounds said opening defined in said tray;

a tool guide having a bore defined therein, said bore of said tool guide being aligned with said opening of said tray so that a tool may be advanced through said bore of said tool guide and said opening of said tray to cut a hole in said proximal end of said resected tibia when said tray contact portion of said evaluation member is positioned away from said opening of said tray; and a trial insert having a recess configured to receive said insert contact portion of said evaluation member.

2. The assembly of claim 1, wherein said insert contact portion of said evaluation member and said recess of said trial insert are configured to enable movement of said trial insert relative to said evaluation member when said insert contact portion is located within said recess.

3. The assembly of claim 2, wherein said insert contact portion of said evaluation member and said recess of said trial insert are configured to enable rotation of said trial insert relative to said evaluation member when said insert contact portion is located within said recess.

4. The assembly of claim 1, wherein said insert contact portion of said evaluation member and said recess of said trial insert are configured to prevent movement of said trial insert relative to said evaluation member when said insert contact portion is located within said recess.

5. The assembly of claim 1, wherein said evaluation member includes a number of spikes which are configured to be driven into said proximal end of said resected tibia to thereby affix said evaluation member to said resected tibia.

6. The assembly of claim 1, further comprising a number of fixation pins, wherein:

said tray has a number of holes defined therein, and said fixation pins respectively extend through said number of holes and into said proximal end of said resected tibia to thereby affix said tray to said resected tibia.

7. The assembly of claim 1, wherein:

said opening of said tray possesses a first profile, said tray contact portion of said evaluation member possesses a second profile, and said first profile is complimentary to said second profile, whereby rotational movement of said evaluation member relative to said tray is inhibited.

8. A prosthesis evaluation assembly, comprising:

a tray configured to be supported on a proximal end of a resected tibia, said tray having a rim structure that defines a tool opening, in said tray;

an evaluation member having (i) a lower portion positioned in mating contact with said rim structure of said tray, and (ii) an upper portion configured to support a trial insert thereon, wherein no portion of said evaluation member extends vertically below said tool opening defined in said tray when said lower portion is positioned in mating contact with said rim structure of said tray; and a tool guide paying a bore defined therein, said bore of said tool guide being aligned with said opening of said tray so that a tool may be advanced through said bore of said tool guide and said opening of said tray to cut a hole in said resected tibial surface when said lower portion of said evaluation member is positioned away from said rim structure of said tray, wherein said evaluation member includes a number of spikes which are configured to be driven into said proximal end of said tibia to thereby affix said evaluation member to said resected tibia.

9. The assembly of claim 8, wherein:

said rim structure of said tray that defines said tool opening possesses a first profile, said lower portion of said evaluation member possesses a second profile, and said first profile is complimentary to said second profile.

10. A surgical procedure, comprising the steps of;

(a) resecting a proximal portion of a tibia so as to form a resected tibial surface:

(b) placing a trial tray on said resected tibial surface, said trial tray having an opening defined therein:

(c) positioning an evaluation member so that a lower end thereof is located within said opening of said trial tray:

(d) positioning a trial insert so that a recess defined therein receives an upper portion of said evaluation member while said lower end of said evaluation member is located within said opening defined in said trial tray;

(e) manipulating said tibia so as to determine stability and kinematics of said trial insert after step (d) and while said lower end of said evaluation member is located within said opening defined in said trial tray;

(f) removing said lower end of said evaluation member from said opening of said trial tray after step (e);

(g) positioning a tool guide so that a bore defined therein is aligned with said opening of said trial tray after step (f); and (h) advancing a tool through said bore of said drill guide and said opening of said trial tray to cut a hole in said tibia after step (g), wherein step (e) is performed while no portion of said evaluation member is positioned distal to said opening defined in said trial tray.

11. A surgical procedure, comprising the steps of:

(a) resecting a proximal portion of a tibia so as to form a resected tibial surface;

(b) placing a trial tray on said resected tibial surface, said trial tray having an opening defined therein;

(c) positioning an evaluation member so that a lower end thereof is located within said opening of said trial tray;

(d) positioning a trial insert so that a recess defined therein receives an upper portion of said evaluation member while said lower end of said evaluation member is located within said opening defined in said trial tray;

(e) manipulating said tibia so as to determine stability and kinematics of said trial insert after step (d) and while said lower end of said evaluation member is located within said opening defined in said trial tray;

(f) removing said lower end of said evaluation member from said opening of said trial tray after step (e);

(g) positioning a tool guide so that a bore defined therein is aligned with said opening of said trial tray after step (f); and (h) advancing a tool through said bore of said drill guide and said opening of said trial tray to cut a hole in said tibia after step (g), wherein step (e) is performed while the entirety of said evaluation member is positioned proximal to said resected tibial surface.

12. The surgical procedure of claim 11, wherein:
said tool guide includes a drill guide, and
said tool includes a drill.

13. The surgical procedure of claim 11, further comprising the step of securing said trial tray to said resected tibial surface after step (b) and before step (c).

14. The surgical procedure of claim 11, further comprising the steps of:

(i) if said stability and/or kinematics of said trial insert is determined insufficient in step (e), positioning an alternate trial insert so that an alternate recess defined therein receives said upper portion of said evaluation member; and (i) manipulating said tibia so as to determine stability and kinematics of said alternate trial insert after step (i).

15. The surgical procedure of claim 11, further comprising the step of affixing said evaluation member to said resected tibial surface after step (b).

* * * * *